(12) United States Patent
Liang et al.

(10) Patent No.: US 9,610,281 B2
(45) Date of Patent: Apr. 4, 2017

(54) USE AND PREPARATION METHOD OF BERBERINE COMPOUNDS

(71) Applicants: Dalian Institute of Chemical Physics, Chinese Academy of Sciences, Dalian, Liaoning (CN); UNIVERSITY OF CALIFORNIA, IRVINE, Irvine, CA (US)

(72) Inventors: Xinmiao Liang, Liaoning (CN); Chaoran Wang, Liaoning (CN); Xiuli Zhang, Liaoning (CN); Yan Zhang, Irvine, CA (US); Zhiwei Wang, Irvine, CA (US); Olivier Civelli, Irvine, CA (US); Yanxiong Ke, Liaoning (CN); Lien Wang, Irvine, CA (US)

(73) Assignees: DALIAN INSTITUTE OF CHEMICAL PHYSICS, CHINESE ACADEMY OF SCIENCES, Dalian (CN); UNIVERSITY OF CALIFORNIA, IRVINE, Irvine, CA (US)

(*) Notice: Subject to any disclaimer, the term of this patent is extended or adjusted under 35 U.S.C. 154(b) by 0 days.

(21) Appl. No.: 14/411,872

(22) PCT Filed: Nov. 19, 2012

(86) PCT No.: PCT/CN2012/084822
§ 371 (c)(1),
(2) Date: Dec. 29, 2014

(87) PCT Pub. No.: WO2014/075309
PCT Pub. Date: May 22, 2014

(65) Prior Publication Data
US 2015/0164870 A1    Jun. 18, 2015

(51) Int. Cl.
*C07D 455/03*    (2006.01)
*A61K 31/4375*    (2006.01)

(52) U.S. Cl.
CPC ........ *A61K 31/4375* (2013.01); *C07D 455/03* (2013.01)

(58) Field of Classification Search
None
See application file for complete search history.

(56) References Cited

FOREIGN PATENT DOCUMENTS

| CN | 101843618 A | 9/2010 |
|---|---|---|
| CN | 102250087 A | 11/2011 |
| CN | 102285981 A | 12/2011 |

OTHER PUBLICATIONS

Wang et al., 396(5) Analytical & Bioanalytical Chem. 1731-1740 (2010) (CAS Abstract).*
Zhang-Ze Ma et al., 13 Molecules 2303-2312 (2008).*
Nagai et al., 4(1) Pharm Tech Japan 37-43 (1988) (CAS Abstract).*

* cited by examiner

*Primary Examiner* — Timothy R Rozof
(74) *Attorney, Agent, or Firm* — Enshan Hong; VLP Law Group LLP

(57) ABSTRACT

A method of treating nervous system diseases associated with dopamine receptors comprising administering a patent in need a compound having a structure of general formula (I) or a pharmaceutical acceptable salt, hydrate, or solvate thereof in a pharmaceutically effective amount, and a method of making the compound having the structure of general formula (I) or a pharmaceutical acceptable salt, hydrate, or solvate thereof. The compound of formula (I) has multiple pharmacological functions such as the functions of activating opioid receptors and blocking dopamine D2 receptors, and has good physicochemical properties and oral bioavailability. General animal experiments show that such a compound has significant and long-lasting analgesic and calming effects and can be used to treat pain and other mental illnesses.

3 Claims, 3 Drawing Sheets

USE AND PREPARATION METHOD OF BERBERINE COMPOUNDS

PRIORITY CLAIM

This is a U.S. National Stage of application No. PCT/CN2012/084822, filed on Nov. 19, 2012.

TECHNICAL FIELD OF THE INVENTION

The present invention relates to the field of medicinal chemistry and pharmacotherapeutics, and more specifically, to the use of a category of quaternary ammonium type berberine derivatives in the preparation of drugs for treating nervous system diseases and their preparation methods.

BACKGROUND OF THE INVENTION

As a symptom exhibited by many diseases, pain is a reaction when adverse stimulation or damage occurs to the body, which can prevent the body from being harmed. But intense pain such as myocardial infarction, advanced cancer, and trauma may not only afflict the patients, but cause severe disorders to their physiological functions, or even shock and death. Therefore, it is necessary to apply painkillers to reduce harm and improve patients' quality of life.

Currently, analgesics clinically used can be divided mainly into narcotic analgesics (opioid analgesics) and non-narcotic analgesics (antipyretic analgesics), in which, the former have stronger effects but with a series of adverse reactions like addiction, drug resistance, respiratory depression, nausea and constipation, especially limitations on the use of such drugs due to possible opioid abuse and the generation of drug dependence. Though with fewer side effects, the latter just exhibit quite limited analgesic effects in general. On the whole, these known analgesics are still not desirable at present; thus, it is valuable to develop a new generation of analgesics that have good analgesic activity but without addiction.

As the dry tuber of papaveraceae corydalis yanhusuo and with the effects of blood activation, qi invigoration and pain relief, *Corydalis yanhusuo* is commonly applied in treating diseases like chest and hypochondriac pain, abdominal pain, amenorrhea and dysmenorrhea, postpartum blood stasis as well as swelling and pain due to falling and contusions, which is a famous analgesic traditional Chinese medicine with a long medicinal history. In the 1950s and 1960s, Jin Guozhang et al. had conducted systematic research on the neuropharmacology of *Corydalis yanhusuo* and found out that it had a series of tertiary amine type alkaloids which boasted analgesic activity, including corydaline, tetrahydropalmatine, protopine and corydalis L, etc. Wherein, with the strongest analgesic effect, L-tetrahydropalmatine (1-THP) was recognized as the main effective component in *Corydalis yanhusuo*'s analgesic effect. Its analgesic effect was weaker than pethidine but stronger than antipyretic analgesics, and particularly, 1-THP had good effects on chronic and persistent dull pain. After that, 1-THP was further discovered to have a significant calming effect, showing the potential for treating nervous system diseases such as schizophrenia. The analgesic effect of 1-THP has no relation to opioid receptors or the prostaglandin system, whose mechanism of action is greatly different from that of narcotic analgesics and antipyretic analgesics. In 1977, 1-THP, as a new drug belonging to those with analgesic and sleep-conducive effects, was incorporated into the Pharmacopoeia of the People's Republic of China (PPRC), mainly used for dull pain, headaches, dysmenorrhea and labor pain, etc. resulting from gastrointestinal and hepatobilliary system diseases, as well as other medical diseases, which features low toxicity, high safety and no addiction, becoming the first nervous system drug successfully developed by the application of modern science and technology since the establishment of the People's Republic of China and also an example of sorting out Chinese medicine through science successfully. However, until the late 1980s, Jin Guozhang et al. did not prove that 1-THP's analgesic and calming effects were related to its blocking activity to dopamine D2 receptor. The blocking effect covers two target areas, specifically, it blocks postsynaptic D2 receptors in the nucleus accumbens (Nac) target area to inhibit the effect of dopamine transporter (DAT), while blocking D2 receptors in the hypothalamic arcuate nucleus (Arc) target area, which can increase the function of endogenous opioid peptides (END) of periaqueductal gray (PAG). Since the dopamine receptors of Nac are the common target area for addiction to opioids, cocaine, and amphetamines, the blocking effect of 1-THP's dopamine D2 receptor can also be used for drug addiction prevention and withdrawal. Over recent years, the practice of 1-THP in preventing the said three drugs has achieved some satisfactory achievements via fundamental and clinical research at home and abroad, which exhibits good potential.

Apart from tertiary amine type berberine, *Corydalis yanhusuo* also contains many quaternary ammonium type berberine compounds, such as dehydrocorydaline, palmatine, berberine and jatrorrhizine, which have been reported on their activities in aspects such as anti-gastric ulcers, anti-bacteria, hypoglycemic effect, and anti-tumor. But so far, there has been no report saying that quaternary ammonium type berberine has analgesic activity.

From our multi-model systematic screen of *Corydalis yanhusuo*'s analgesic activity, it is discovered that some quaternary ammonium type berberines have dopamine D2 receptor blocking activity. Among them, the dehydrocorybulbine (DHCB) further contains weak opioid receptor activity, for which related animal experiments indicate that its analgesic and calming activities are stronger than those of 1-THP, while the acting duration and the drug resistance property are superior to that of morphine, which has good prospect in the application of analgesia. In addition, due to its dopamine receptor activity similar to that of 1-THP, other nervous system diseases associated with dopamine receptor system such as depression and drug addiction can be predicted, which is promising as well.

SUMMARY OF THE INVENTION

The present invention provides the use of a compound with the structure of general formula (I) or its medicinal salts, hydrates or solvates:

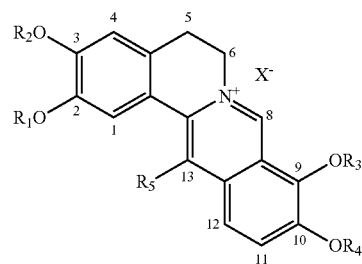

wherein, $R_1$ and $R_2$ are H or $C_1$-$C_6$ linear or branched chain alkyls, $C_1$-$C_6$ halogenated linear or branched chain alkyls, or $C_1$-$C_6$ acyl and aryl respectively, or $R_1$ and $R_2$ connect to form —$CH_2$—;

$R_3$ and $R_4$ are H or $C_1$-$C_6$ linear or branched chain alkyls, $C_1$-$C_6$ halogenated linear or branched chain alkyls, or $C_1$-$C_6$ acyl and aryl respectively, or $R_3$ and $R_4$ connect to form —$CH_2$—;

$R_5$ is H or $C_1$-$C_6$ linear or branched chain alkyl, $C_1$-$C_6$ halogenated linear or branched chain alkyl, or $C_1$-$C_6$ acyl or aryl; and $X^-$ is an anion selected from a halide ion and carboxylate radical in preparing drugs for nervous system diseases related to dopamine receptor.

In the present invention, the nervous system disease related to dopamine receptors is pain or depression.

In a preferred embodiment of the present invention, $R_1$ and $R_2$ are H or $C_1$-$C_6$ linear or branched chain alkyls respectively, or $R_1$ and $R_2$ connected to form —$CH_2$—; $R_3$ and $R_4$ are H or $C_1$-$C_6$ linear or branched chain alkyls respectively; $R_5$ is H or $C_1$-$C_6$ linear or branched chain alkyl; $X^-$ is an anion selected from halide ion and carboxylate radical.

Preferably, the berberine derivatives of the present invention are the compounds shown in 1~20 of the following table:

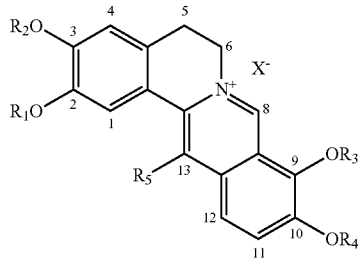

| Compound | $R_1$ | $R_2$ | $R_3$ | $R_4$ | $R_5$ | X |
|---|---|---|---|---|---|---|
| 1 | —$CH_2$— | | CH3 | CH3 | H | $Cl^-$ |
| 2 | —$CH_2$— | | CH3 | CH3 | CH3 | $Cl^-$ |
| 3 | —$CH_2$— | | H | CH3 | H | $HCOO^-$ |
| 4 | —$CH_2$— | | H | CH3 | CH3 | $HCOO^-$ |
| 5 | H | H | H | CH3 | H | $Cl^-$ |
| 6 | H | H | H | CH3 | CH3 | $Cl^-$ |
| 7 | H | H | CH3 | CH3 | H | $Cl^-$ |
| 8 | H | H | CH3 | CH3 | CH3 | $Cl^-$ |
| 9 | H | CH3 | CH3 | CH3 | H | $HCOO^-$ |
| 10 | H | CH3 | CH3 | CH3 | CH3 | $HCOO^-$ |
| 11 | CH3 | H | CH3 | CH3 | H | $HCOO^-$ |
| 12 | CH3 | H | CH3 | CH3 | CH3 | $HCOO^-$ |
| 13 | H | CH3 | H | CH3 | H | $HCOO^-$ |
| 14 | H | CH3 | H | CH3 | CH3 | $HCOO^-$ |
| 15 | CH3 | H | H | CH3 | H | $HCOO^-$ |
| 16 | CH3 | H | H | CH3 | CH3 | $HCOO^-$ |
| 17 | CH3 | CH3 | CH3 | CH3 | H | $HCOO^-$ |
| 18 | CH3 | CH3 | CH3 | CH3 | CH3 | $HCOO^-$ |
| 19 | CH3 | CH3 | H | CH3 | H | $HCOO^-$ |
| 20 | CH3 | CH3 | H | CH3 | CH3 | $HCOO^-$ |

The present invention further relates to a method for preparing a compound with the structure of general formula (I) or its medicinal salts, hydrates or solvates, comprising protecting a hydroxyl of a compound of formula II as shown above at positions 2 or 3 by introducing protecting group $R_6$ or $R_7$, reacting the other hydroxyl with a halohydrocarbon, sulphonate, acyl chloride, anhydride or sulfonyl chloride to introduce $R_1$ or $R_2$, obtaining a mono-hydroxyl compound after deprotection, reacting the mono-hydroxyl with a halohydrocarbon, sulphonate, acyl chloride, anhydride or sulfonyl chloride to introduce the other $R_1$ or $R_2$ and obtaining the compound of formula (I), wherein $R_1$, $R_2$, $R_3$, $R_4$, 5, and $X^-$ are as defined by claim 1; $R_6$ and $R_7$ are protecting groups of a phenolic hydroxyl group.

In the method of the present invention, $R_6$ is methoxyl methyl (MOM) or benzyloxy methyl (BnOCH2), and $R_7$ is the protecting group of silane selected from trimethylsilane (TMS), triethylsilane (TES), tert-butyldiphenylsilane (TBDPS), tert-butyldimethylsilane (TBDMS), diisopropylsilane (DIPS), diphenylsilane (DPS) and 1,1,3,3-tetraisopropyldisiloxane (TIPDS).

The berberine derivatives or their physiologically acceptable salts of the present invention can be obtained not only by extraction and separation from plants rich in berberine compounds like Corydalis yanhusuo, Coptis chinensis and Cortex Phellodendri, but also by semi-synthesis via the following reaction in the way of taking cheap natural or synthetic berberine as the starting material:

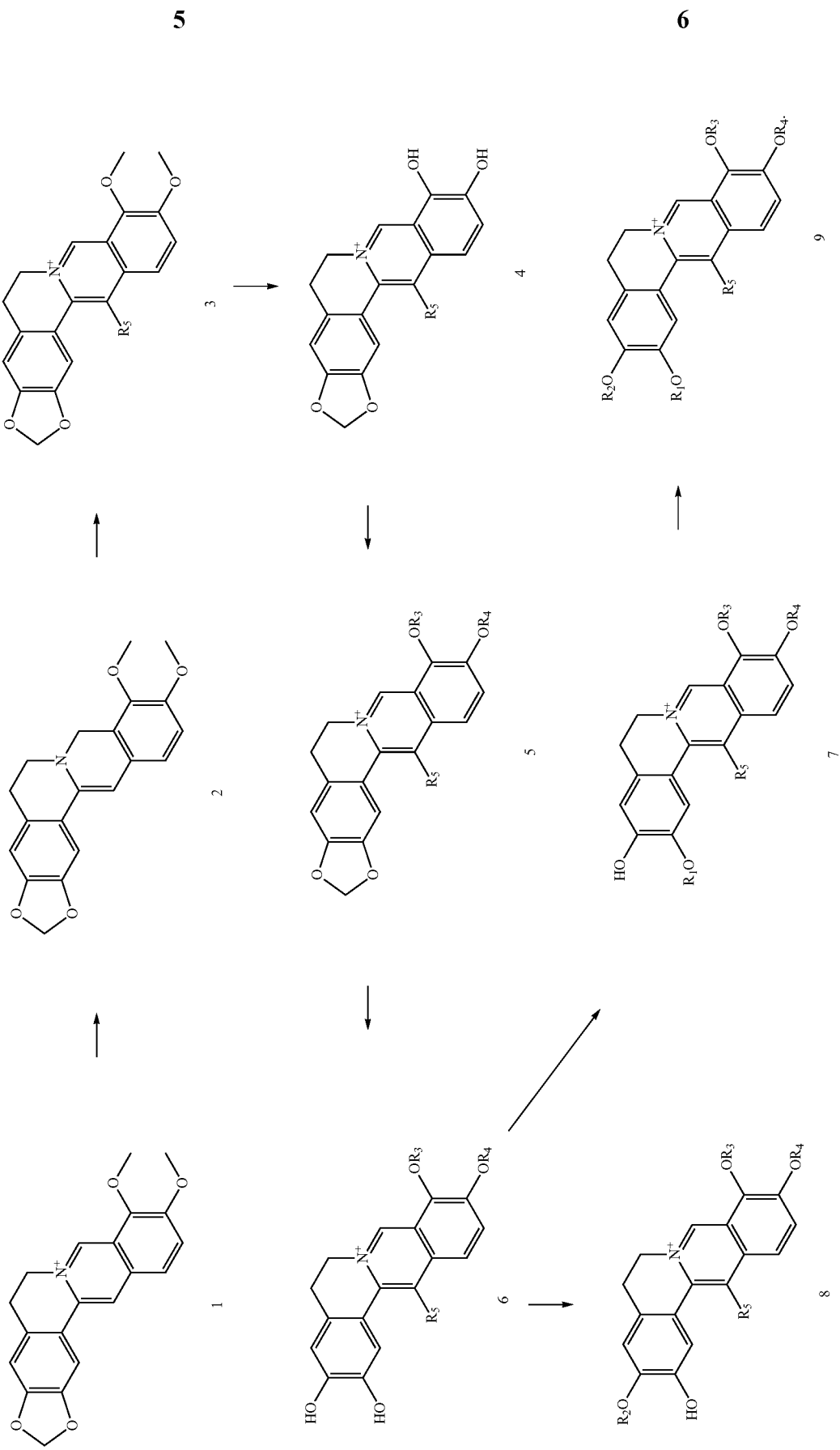

Wherein, the synthesis from raw material 1 to key intermediate 6, which has been reported in many literatures, can be realized through multiple reaction routes. To describe the related art better, the present invention lists a simple realization method as shown in the drawing above, but does not set up a claim to patent protection, nor limit application in other ways of the patent.

In the above route, dissolve hydrochloric acid or sulfuric acid berberine in methanol, then under an alkaline environment, dihydroberberine can be obtained after sodium borohydride or potassium borohydride reduction; the compound reacts with various aldehydes, halohydrocarbons, or acyl chlorides via heating in acidic ethanol to generate corresponding substituted berberine with 13-alkyl or aryl or acyl, namely, $R_5$ is the berberine derivatives with H or $C_1$-$C_6$ linear or branched chain alkyl, $C_1$-$C_6$ halogenated linear or branched chain alkyl, or $C_1$-$C_6$ acyl or aryl; decompose such compounds through a vacuum under high temperature to make methoxyls at positions 9 and 10 crack and form hydroxyls, which react with an acyl chloride, anhydride, sulfonyl chloride or sulfonic anhydride reagent in the presence of an acid receptor, after which $R_3$ and $R_4$ can be obtained as corresponding alkyl, acyl or aryl derivatives; further, hydrolyze hemiacetals at positions 2 and 3 in 60% sulfuric acid with the catalysis of phloroglucinol to generate dihydric berberine derivatives, namely the key intermediate 6 used in the present invention.

One of the purposes of the present invention is to propose a preparation method of using certain protecting groups respectively to provide selective monoprotection for the dihydroxyl on the compound 6 through the intermediate 6, making the remaining hydroxyls react with reagents such as halohydrocarbon, sulphonate, acyl chloride, acyl chloride and sulfonyl chloride, and after deprotection, obtaining corresponding $R_1$ or $R_2$ substituted compound 7 or 8, which can further react with the above-mentioned reagents to obtain 9.

ADVANTAGES OF THE INVENTION

Proceeding from the quarternary ammonium type berberine compounds with analgesic activity which are obtained by extraction and separation from plants, the present invention designs and synthesizes a series of berberine derivatives that act on opioid receptors and dopamine receptors. The general animal experiments show that such compounds have a significant and long-acting analgesic effect as well as calming effect, and can be used to treat pain or other nervous system diseases related to dopamine receptor activity. The compounds of the present invention boast simple synthesis, easy preparation, and rich synthetic raw materials.

DETAILED DESCRIPTION OF THE PRESENTLY PREFERRED EMBODIMENTS

Figure 1:
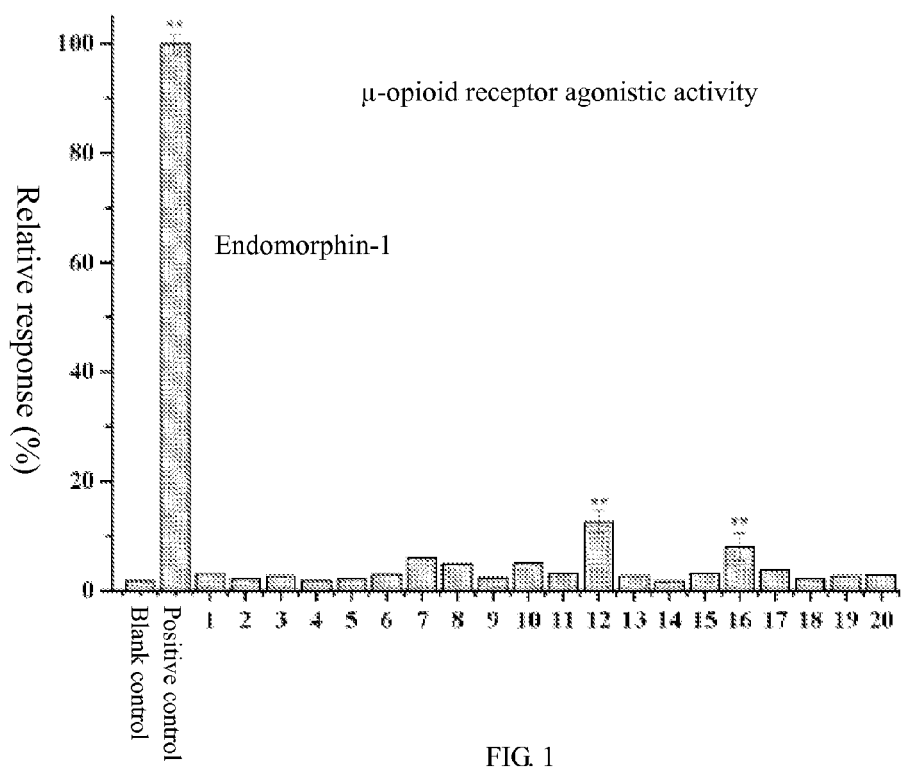
FIG. 1 illustrates the agonist on μ opioid receptor of the compounds of the present invention.

The present invention will be further illustrated in combination with the embodiments hereinafter, which, however, do not constitute any limitation on the present invention. In the preparation embodiments as below, $^1$H-NMR is determined by a Varian Mercury AMX 600 MHz type nuclear magnetic resonance instrument; chemical shift is expressed by δ (ppm); the reverse-phase preparative column for separation is C18HCE (20×250 mm, 10 um), which is purchased from Acchrom Technologies Co., Ltd., Zhejiang Province; and the mobile phase systems applied are acetonitrile and 0.1% formic acid solution.

Preparation Embodiments

Preparation of Compound 2:

Dissolve 5 g of hydrochloric acid berberine in 400 ml methanol, add 5 g of anhydrous potassium carbonate, drop 6 ml 5% sodium hydroxide solution (containing 0.4 g of sodium borohydride), stir up under room temperature for one-hour reaction, filter the precipitations out, wash them with 30% and 80% ethanol and put them into methanol for recrystallization, then obtain dihydroberberine (3.5 g, 76%). Dissolve dihydroberberine in 100 ml 80% mixture of ethanol and glacial acetic acid, add 40 ml of formalin to produce reflux reaction under 85~95° C. for 4~5 hours, carry out rotary evaporation to eliminate organic solvents, add appropriate concentrated hydrochloric acid to the remnants, churn up for an hour under room temperature, filter the solids out, wash them with a small quantity of water and methanol, put them into the methanol for recrystallization, finally obtain compound 2 (3.6 g, 90%).

Compound 2, $C_{21}H_{20}NO_4Cl$, MW: 385.5, yellow crystal, easily soluble in methanol.

$^1$H NMR(600MHz,DMSO-d6): δ 9.92 (1H, s, H-8), 8.21 (1H, d, J=9.6Hz, H-12), 8.17 (1H, d, J=9.6Hz, H-11), 7.47 (1H, s, H-1), 7.15 (1H, s, H-4), 6.18 (2H, s, —OCH$_2$O—), 4.84 (2H, t, H-6), 4.09 (3H, s, —OCH3), 4.08 (3H, s, —OCH3), 3.15 (2H, t, H-5), 2.92 (3H, s, —CH3).

Preparation of Compound 3:

Put hydrochloric acid berberine (1.50 g, 4.0 mmol) in a 100 ml round-bottom flask, maintain the vacuum degree (20~30 mmHg) of the reaction system with an oil pump, heat up to 200° C. and keep the reaction for 20 mins, after the temperature drops to room temperature, stop the operation of the vacuum pump. The reaction product is purified by preparative reversed-phase chromatography with $C_{18}$, finally compound 3 (0.92 g, 62%) is obtained.

Compound 3, $C_{19}H_{15}NO_4COOH$, MW: 367.35, brownish red powder, easily soluble in methanol.

$^1$H NMR(600MHz,DMSO-d6): δ 9.06 (1H, s, H-8), 8.60 (1H, s, H-13), 8.18 (1H, d, J=9.6 Hz, H-12), 8.10 (1H, d, J=9.6 Hz, H-11), 7.47 (1H, s, H-1), 6.87 (1H, s, H-4), 6.10 (2H, s, —OCH2O—), 4.84 (2H, t, H-6), 4.63 (3H, s, OMe-10), 3.15 (2H, t, H-5).

Preparation of Compound 4:

Put compound 2 (1.50 g, 3.9 mmol) in a 100 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 4 (0.73 g, 68%) is obtained.

Compound 4, $C_{20}H_{17}NO_4COOH$, MW: 381.38, brownish red powder, easily soluble in methanol.

$^1H$ NMR (600 MHz,DMSO-d6): δ 9.26 (1H, s, H-8), 8.14 (1H, d, J=9.6Hz,H-12), 8.06 (1H, d, J=9.6Hz, H-11), 7.40 (1H, s, H-1), 6.82(1H, s, H-4), 6.07 (2H, s, —OCH$_2$O—), 4.84 (2H, t, H-6), 4.63 (3H, s, OMe-10), 3.15 (2H, t, H-5), 2.42 (3H, s, —CH3).

Preparation of Compound 5:

Add 5 g of phloroglucinol to 100 ml 60% sulfuric acid (v/v) stepwise, stir up to dissolve it into colorless solution, add hydrochloric acid berberine (5.0 g, 13.4 mmol), after 15~20 min of reaction by oil bath under 90~95° C., pour the solution to 100 ml concentrated brine, cool it to room temperature with agitation, filter the precipitations out, recrystallize in methanol for two-times, finally obtain compound 5 (2.2 g, 45%).

Compound 5, $C_{19}H_{18}NO_4Cl$, MW: 359.8, yellow powder, easily soluble in methanol.

$^1H$ NMR(600MHz,DMSO-d6): δ 9.67 (1H, s, H-8), 8.62 (1H, s, H-13), 8.07 (1H, d, J=9Hz,H-12), 7.95 (1H, d, J=9Hz,H-11), 7.43 (1H, s, H-1), 6.59 (1H, s, H-4), 4.82 (2H, t, H-6), 4.06 (3H,s,—OCH3), 4.08 (3H, s, —OCH3), 3.04 (2H,t,H-5).

Preparation of Compound 6:

Add 5 g of phloroglucinol to 100 ml 60% sulfuric acid (v/v) stepwise, stir up to dissolve it into colorless solution, add compound 2 (5.0 g, 13.0 mmol), after 15~20 min of reaction by oil bath under 90~95° C., pour the solution to 100 ml concentrated brine, cool it to room temperature with agitation, filter the precipitations out, recrystallize in methanol for two-times, finally obtain compound 6 (1.8 g, 37%).

Compound 6, $C_{20}H_{20}NO_4Cl$, MW: 373.5, yellow powder, easily soluble in methanol.

$^1H$ NMR(600MHz,DMSO-d6): δ 9.57 (1H, s, H-8), 8.02 (Lh, d, J=9.0Hz, H-12), 7.92 (1H, J=9.0Hz,H-11), 6.91 (1H, s, H-1), 6.24 (1H, s, H-4), 4.65 (2H, t, H-6), 4.01 (3H, s, —OCH3), 4.00 (3H, s, —OCH3), 2.83 (2H, t, H-5), 2.80 (3H, s, —CH3).

Preparation of Compound 7:

Put compound 5 (100 mg, 0.28 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 7 (52 mg, 54%) is obtained.

Compound 7, $C_{19}H_{15}NO_4COOH$, MW: 367.35, brownish red powder, easily soluble in methanol.

$^1H$ NMR(600MHz,DMSO-d6): δ 9.67 (1H, s, H-8), 8.62 (1H, s, H-13), 8.07 (1H, d, J=9Hz, H-12), 7.95 (1H, J=9Hz, H-11), 7.43 (1H, s, H-1), 6.59 (1H, s, H-4), 4.82 (2H, t, H-6), 4.06 (3H, s, —OCH3), 3.04 (2H, t, H-5).

Preparation of Compound 8:

Put compound 6 (100 mg, 0.27 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 7 (40 mg, 41%) is obtained.

Compound 8, $C_{20}H_{17}NO_4COOH$, MW: 381.35, brownish red powder, easily soluble in methanol.

$^1H$ NMR(600MHz,DMSO-d6): δ 9.57 (1H, s, H-8), 8.02 (1H, d, J=9.0Hz, H-12), 7.92 (1H, J=9.0Hz,H-11), 6.91 (1H, s, H-1), 6.24(1H, s, H-4), 4.65 (2H, t, H-6), 4.01 (3H, s, —OCH3), 2.83 (2H, t, H-5), 2.80 (3H, s, —CH3).

Preparation of Compound 9:

Mix compound 5 (3 g, 8.3 mmol) with 3 g of anhydrous potassium carbonate, put the mixture in a 500 ml three-neck flask, add 300 ml of dry DMF and dissolve it by agitation, put the solution in an ice bath and supply nitrogen for protection, drop 2.7 ml of tert-butyldiphenylchlorosilane (TBDPSC1, 2.85 g, 10.4 mmol), after that, continue to beat up and keep the reaction for 10 min, add p-tolyl methyl sulfonate (1.90 g, 10.2 mmol) and 80% NaH (0.3 g), keep the reaction in 40° C. warm water for 2 hours, after being purified by preparative chromatography, the reaction solution is concentrated under vacuum, finally the formate (2.05 g, 64%) of compound 11 is obtained.

Compound 9, $C_{20}H_{20}NO_4COOH$, MW: 383.4, yellow crystal, easily soluble in methanol.

$^1H$ NMR(600MHz,DMSO-d6): δ 9.82 (1H, s, H-8), 8.75 (1H, s, H-13), 8.13 (1H, d, J=9Hz, H-12), 8.00 (1H, d, J=9Hz, H-11), 7.57 (1H, s, H-1), 7.00 (1H, s, H-4), 4.89 (2H, t, H-6), 4.06 (3H, s, —OCH3), 4.03 (3H, s, —OCH3), 3.85 (3H, s, —OCH3), 3.14 (2H, t, H-5).

Preparation of Compound 10:

Mix compound 6 (3 g, 8.3 mmol) with 3 g of anhydrous potassium carbonate, put the mixture in a 500 ml three-neck flask, add 300 ml of dry DMF and dissolve it by agitation, put the solution in an ice bath and supply nitrogen for protection, drop 2.7 ml of tert-butyldiphenylchlorosilane (TBDPSC1, 2.85 g, 10.4 mmol), after that, continue to beat up and keep the reaction for 10 min, add p-tolyl methyl sulfonate (1.90 g, 10.2 mmol) and 80% NaH (0.3 g), keep the reaction in 40° C. warm water for 2 hours, after being purified by preparative chromatography, the reaction solution is concentrated under vacuum, finally compound 11 (2.17 g, 68%) is obtained.

Compound 10, $C_{21}H_{22}NO_4COOH$, MW: 397.4, yellow crystal, easily soluble in methanol.

$^1H$ NMR(600MHz,DMSO-d6): δ 9.86 (1H,s,H-8), 8.20 (1H, d, J=9.2Hz, H-12), 8.16 (1H, d, J=9Hz, H-11), 7.36 (1H, s, H-1), 6.92 (1H, s, H-4), 4.82 (2H, t, H-6), 4.10 (3H, s, —OCH3), 4.09 (3H, s, —OCH3), 3.87 (3H, s, —OCH3), 3.07 (2H, t, H-5), 2.98 (3H, s, —CH3).

Preparation of Compound 11:

Mix compound 5 (3 g, 8.3 mmol) with 3 g of anhydrous potassium carbonate, put the mixture in a 500 ml three-neck flask, add 300 ml of dry DMF and dissolve it by agitation, put the solution in an ice bath and supply nitrogen for protection, drop 0.8 ml of chloromethyl ether (0.85 g, 10.5 mmol) group by group, after that, continue to beat up and keep the reaction for 30 min, add p-tolyl methyl sulfonate (1.90 g, 10.2 mmol) and 80% NaH (0.3 g), keep the reaction in 40° C. warm water for 2 hours, after being purified by preparative chromatography, the reaction solution is concentrated under vacuum, finally compound 11 (1.63 g, 51%) is obtained.

Compound 11, $C_{20}H_{20}NO_4COOH$, MW: 383.4, yellow crystal, easily soluble in methanol.

$^1H$ NMR(600MHz,DMSO-d6): δ 9.84 (1H, s, H-8), 8.77 (1H, s, H-13), 8.15 (1H, d, J=9.0Hz, H-12), 8.02 (1H, J=9.0Hz, H-11), 7.56 (1H, s, H-1), 6.92 (1H, s, H-4), 4.82 (2H, t, H-6), 4.10 (3H, s, —OCH3), 4.09 (3H, s, —OCH3), 3.87 (3H,s,—OCH3), 3.07 (2H, t, H-5).

Preparation of Compound 12:

Mix compound 6 (3 g, 8.0 mmol) with 3 g of anhydrous potassium carbonate, put the mixture in a 500 ml three-neck flask, add 300 ml of dry DMF and dissolve it by agitation, put the solution in an ice bath and supply nitrogen for protection, drop 0.8 ml of chloromethyl ether (0.85 g, 10.5 mmol) group by group, after that, continue to beat up and keep the reaction for 30 min, add p-tolyl methyl sulfonate (1.90 g, 10 mmol) and 80% NaH (0.3 g), keep the reaction in 40° C. warm water for 2 hours, after being purified by preparative chromatography, the reaction solution is concentrated under vacuum, finally compound 12 (1.75 g, 55%) is obtained.

Compound 12, $C_{21}H_{22}NO_4COOH$, MW: 397.4 yellow crystal, easily soluble in methanol.

$^1$H NMR(600MHz,DMSO-d6): δ 9.86 (1H,s,H-8), 8.20 (1H, d, J=9.2Hz, H-12), 8.16 (1H, d, J=9Hz, H-11), 7.36 (1H, s, H-1), 6.92 (1H, s, H-4), 4.82 (2H, t, H-6), 4.10 (3H, s, —OCH3), 4.09 (3H, s, —OCH3), 3.87 (3H, s, —OCH3), 3.07 (2H, t, H-5), 2.98 (3H, s, —CH3).

Preparation of Compound 13:

Put compound 9 (100 mg, 0.26 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (45 mg, 47%) is obtained.

Compound 13, $C_{19}H_{18}NO_4COOH$, MW: 369.4, brownish red powder, easily soluble in methanol.

$^1$H NMR(600MHz,DMSO-d6): δ 9.82 (1H, s, H-8), 8.75 (1H, s, H-13), 8.13 (1H, d, J=9Hz, H-12), 8.00 (1H, d, J=9Hz, H-11), 7.57 (1H, s, H-1), 7.00 (1H, s, H-4), 4.89 (2H, t, H-6), 4.06 (3H, s, —OCH3), 3.85 (3H, s, —OCH3), 3.14 (2H, t, H-5).

Preparation of Compound 14:

Put compound 10 (100 mg, 0.25 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (35 mg, 36%) is obtained.

Compound 14, $C_{20}H_{20}NO_4COOH$, MW: 383.4 brownish red powder, easily soluble in methanol.

NMR(600MHz,DMSO-d6): δ 9.86 (1H, d, J=9.2Hz, H-12), 8.16 (1H, d, J=9Hz, H-11), 7.36 (1H, s, H-1), 6.92 (1H, s, H-4), 4.82 (2H, t, H-6), 4.10 (3H, s, —OCH3), 3.87 (3H, s, —OCH3), 3.07 (2H, t, H-5), 2.98 (3H, s, —CH3).

Preparation of Compound 15:

Put compound 11 (100 mg, 0.26 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (55 mg, 57%) is obtained.

Compound 15, $C_{19}H_{18}NO_4COOH$, MW: 369.4, red powder, easily soluble in methanol.

$^1$H NMR(600MHz,DMSO-d6): δ 9.84 (1H, s, H-8), 8.77 (1H, s, H-13), 8.15 (1H, d, J=9.0Hz, H-12), 8.02 (1H, d, J=9.0Hz, H-11), 7.56 (1H, s, H-1), 6.92 (1H, s, H-4), 4.82 (2H, t, H-6), 4.10 (3H, s, —OCH3), 3.87 (3H, s, —OCH3), 3.07 (2H, t, H-5).

Preparation of Compound 16:

Put compound 12 (100 mg, 0.26 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (53 mg, 55%) is obtained.

Compound 16, $C_{20}H_{20}NO_4COOH$, MW: 383.4, red powder, easily soluble in methanol.

$^1$H NMR(600MHz,DMSO-d6): δ 9.86 (1H, s, H-8), 8.20 (1H, d, J=9.2Hz, H-12), 8.16 (1H, d, J=9Hz, H-11), 7.36 (1H, s, H-1), 6.92 (1H, s, H-4), 4.82 (2H, t, H-6), 4.10 (3H, s, —OCH3), 3.87 (3H, s, —OCH3), 3.07(2H, t, H-5), 2.98 (3H, s, —CH3).

Preparation of Compound 17:

Stir and dissolve compound 5 (1.0 g, 2.77 mmol) in 100 ml dry DMF, add anhydrous potassium carbonate (1 g) and 80% NaH (0.3 g), keep the reaction in 40° C. warm water for 2 hours, after being purified by preparative chromatography, the reaction solution is concentrated under vacuum, finally, the formate (0.8 g, 72%) of compound 17 is obtained.

Compound 17, $C_{21}H_{22}NO_4COOH$, MW: 397.4, yellow crystal, easily soluble in methanol.

$^1$H NMR(600MHz,DMSO-d6): δ 9.67 (1H, s, H-8), 8.82 (1H, s, H-13), 8.07 (1H, d, J=9Hz, H-12), 7.85 (1H, d, J=9Hz, H-11), 7.45 (1H, s, H-1), 6.69 (1H, s, H-4), 4.92 (2H, t, H-6), 4.24 (3H, s, —OCH3), 4.08 (3H, s, —OCH3), 4.03 (3H, s, —OCH3), 3.97 (3H, s, —OCH3), 3.24 (2H, t, H-5).

Preparation of Compound 18:

Stir and dissolve compound 6 (1.0 g, 2.67 mmol) in 100 ml dry DMF, add anhydrous potassium carbonate (1 g) and 80% NaH (0.3 g), keep the reaction in 40° C. warm water for 2 hours, after being purified by preparative chromatography, the reaction solution is concentrated under vacuum, finally, the formate (0.7 g, 66%) of compound 18 is obtained.

Compound 18, $C_{22}H_{24}NO_4COOH$, MW: 411.4, yellow crystal, easily soluble in methanol.

$^1$H NMR(600MHz,DMSO-d6): δ 9.87 (1H, s, H-8), 7.95 (1H, d, J=9Hz, H-12), 7.87 (1H, d, J=9Hz, H-11), 7.33 (1H, s, H-1), 6.91(1H, s, H-4), 5.12 (2H, t, H-6), 4.30 (3H, s, —OCH3), 4.08 (3H, s, —OCH3), 4.00 (3H, s, —OCH3), 3.95 (3H, s, —OCH3), 3.34(2H, t, H-5).

Preparation of Compound 19:

Put compound 17 (100 mg, 0.25 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (43 mg, 44%) is obtained.

Compound 19, $C_{20}H_{20}NO_4COOH$, MW: 383.4, red powder, easily soluble in methanol.

$^1$H NMR(600 MHz,DMSO-d6): δ 9.67 (1H, s, H-8),8.82 (1H, s, H-13),8.09 (1H, d, J=9Hz, H-12), 7.85 (1H, d, J=9Hz, H-11), 7.45 (1H, s, H-1), 6.69(1H, s, H-4), 4.92 (2H, t, H-6), 4.24 (3H, s, —OCH3), 4.03 (3H, s, —OCH3), 3.97 (3H, s, —OCH3), 3.24(2H, t, H-5).

Preparation of Compound 20:

Put compound 18 (100 mg, 0.25 mmol) in a 20 ml round-bottom flask, maintain the vacuum degree (20~30 mmHg) of the reaction system with an oil pump, heat up to 200° C. and keep the reaction for 20 min, after the temperature drops to room temperature, stop the operation of the vacuum pump. The reaction product is purified by preparative reversed-phase chromatography with $C_{18}$, finally compound 13 (63 mg, 65%) is obtained.

Compound 20, $C_{21}H_{22}NO_4COOH$, MW: 397.4, red powder, easily soluble in methanol.

$^1H$ NMR(600MHz,DMSO-d6): δ 9.87(1H, s, H-8), 7.95 (1H, d, J=9Hz, H-12), 7.87 (1H, d, J=9Hz, H-11), 7.33 (1H, s, H-1), 6.91(1H, s, H-4), 5.12 (2H, t, H-6), 4.30 (3H, s, —OCH3), 4.00 (3H, s, —OCH3), 3.95 (3H, s, —OCH3), 3.34(2H, t, H-5).

Activity Experiment Embodiments

Activity Example 1: to Make Preliminary Evaluation In Vitro on the Analgesic Effect of Partial Compounds of the Present Invention on Related Receptors by Applying Cell Receptor Models.

Experimental scheme: the cells used to express μ opioid receptors in this research are stably transfected human embryonic kidney 293T cells (HEK293T); the dopamine receptor applied is transiently transfected HEK293T. In this scheme, part of the berberine derivatives obtained in the present invention were added to the cells that have expressed with corresponding receptors, and FLIPR (Fluorometric Imaging Plate Reader; Molecular Devices Corp) was applied to screen and identify their functions. Specifically: inoculate cells to a 96-well cell culture plate coated with poly-D-lysme based on 80,000 per well, after 24 hours, remove the medium, add 100 μl fluorescent dye solution (2 μM Fluo-4 AM dissolves first in pluronic acid and then in the buffer composed of haploid Hank's buffer and 20 mM HEPES, with pH 7.4) to each well and keep it at 37° C. for 1 hour, then wash the cells with the buffer three times. Dissolve the compounds to be tested with DMSO and put them in a 96-well plate, apply FLIPR to automatically add samples to the cell culture plate and incubate for 3 min (for the tests of agonist of μ-opioid receptor) or 10 min (for the tests of antagonist of dopamine receptor). Then perform fluorescence detection under the wavelength of 520 nm and 488 nm, thus monitoring the concentration of $Ca^{2+}$ in the cells. If the response tested increases (as to agonist) or decreases (as to antagonist) comparing with dimethyl sulfoxide (DMSO) blank control and significant difference exists between the two sets of data statistically, it indicates that the compound acts on related receptor.

Figure 2:
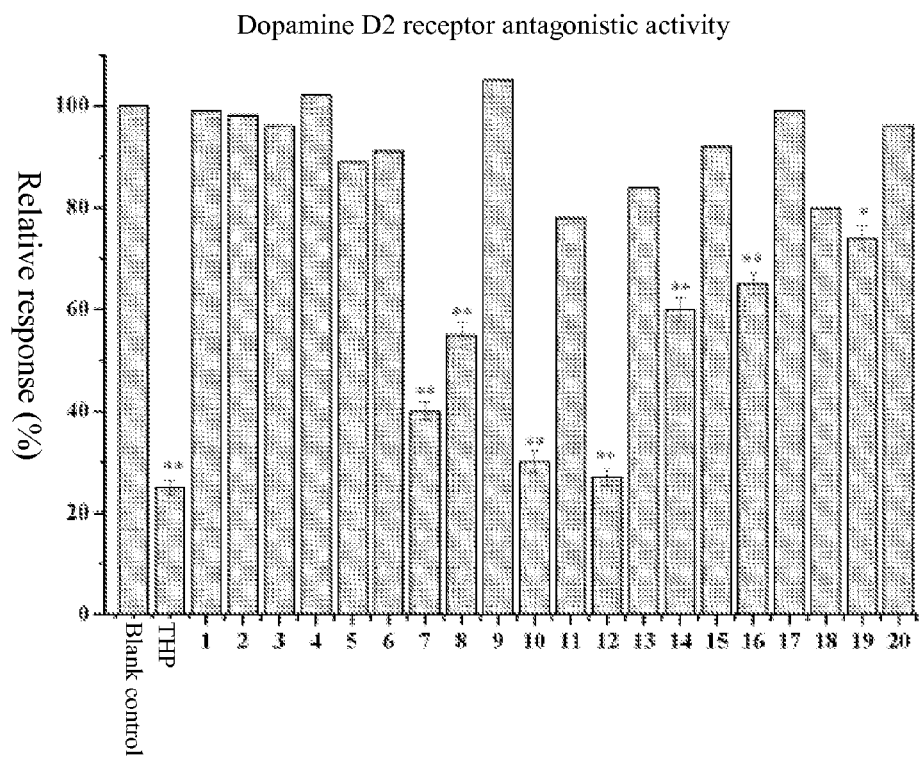
FIG. 2 illustrates the antagonist on dopamine D2 receptor of the compounds of the present invention.

Experimental results: FIG. 1 and FIG. 2 illustrate the effects of partial compounds of the present invention respectively on μ opioid receptor and dopamine receptor models, wherein DMSO is blank control, endomorphin-1 is the positive control of μ opioid receptor's agonist, and THP is the positive control of dopamine D2 receptor's antagonist. The screening results at the cell level show that a part of the compounds obtained in the present invention have a certain agonist over μ opioid receptors (compounds 12 and 16), and besides, some have good antagonist upon dopamine D2 receptors (compounds 7, 8, 10, 12, 14 and 16). As the compound 12(dehydrocorybulbine, DHCB) has higher in vitro activity (antagonist activity on D2 is equivalent to that of THP), and is the first compound with the activity prepared from *Corydalis yanhusuo*, we chose DHCB to perform further activity evaluation and integral pharmacodynamic experiments on animal.

Figure 3:
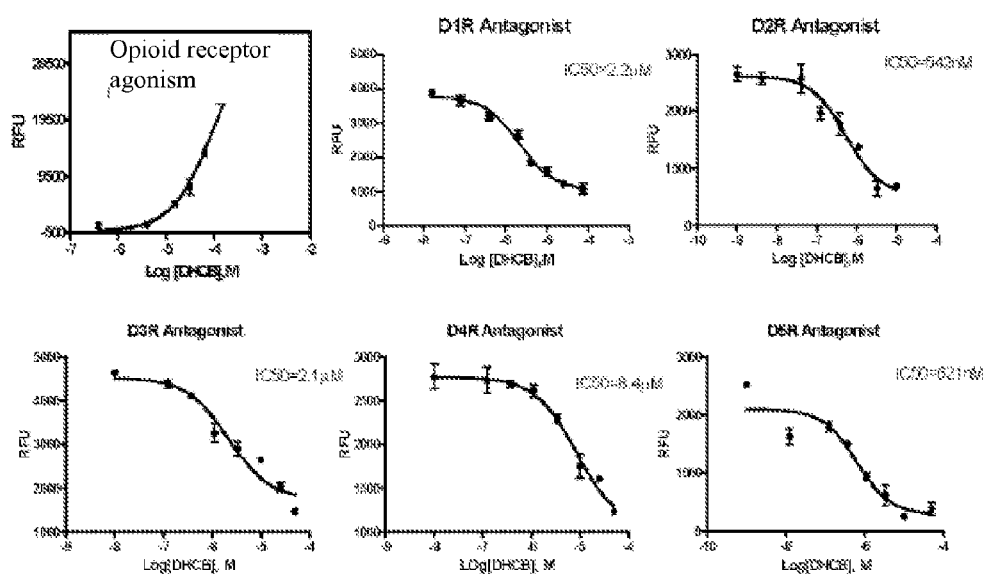
FIG. 3 illustrates the dose-effect curves of the effect of berberine derivative 12 (namely DHCB) on opioid receptor and 5 dopamine receptors.

Activity Example 2: to Compare Dose-effect Curves of Dehydrocorybulbine (DHCB) Effect on the Activities of Various Receptors The experimental scheme is the same as that in example 1, except that when adding, dilute the compounds to be tested with buffer to different concentrations, so as to detect responses under different doses. This method has been used to test DHCB effect on μ-opioid receptors and 5 dopamine receptors, with the results as shown in FIG. 3 and Table 1. The experiments show that, besides being a weak agonist for μ-opioid receptors, DHCB is also an antagonist of multiple dopamine receptors (D1, D2, D3, D4 and D5), which are not only pain-related, but also associated with several mental illnesses such as schizophrenia and depression, indicating that the compound has certain value in therapeutic use concerning this aspect. In addition, μ-opioid receptor's weak synergism can further enhance the analgesic effect of DHCB.

TABLE 1

Comparison of In Vitro Activities of dehydrocorybulbine (DHCB) and L-tetrahydropalmatine (1-THP)

| | Agonist ($EC_{50}$) | | Antagonist ($IC_{50}$) | | |
|---|---|---|---|---|---|
| | μ opioid receptor (μM) | Dopamine D1 (μM) | Dopamine D2 (μM) | Dopamine D3 (μM) | Dopamine D4 (μM) | Dopamine D5 (μM) |
| DHCB | 100 (74~136) | 2.16 (1.4~3.2) | 0.52 (0.24~1.12) | 2.4 (1.3~4.5) | 8.4 (4.6~15) | 0.73 (0.25~2.1) |

Activity Example 3

Thermal Radiation Tail-flick Experiment I in Mice (Tail-flick assay): to Evaluate the Analgesic Effect In Vivo of the Compounds of the Present Invention.

Select CD-1 mice (with the original weight being 30-40 g) and divide them into 6 groups (solvent group, morphine group, 1-THP group and DHCB groups with different doses: 5, 10, and 40 mg/kg), each including 9-11 mice. Place mice tails on the thermal radiation tail-flick apparatus and direct the light beam at ⅓ of the mice tails. First determine the basic pain thresholds of each group of mice, then inject the test samples into the abdominal cavities of the mice respectively, and after 30 min, re-determine the mice's pain thresholds. The irradiation time was no more than 22 sec. See Table 2 for the determination results. The experimental results show that, DHCB has significant dose-dependent analgesic effect under the doses of 5, 10, and 40 mg/kg. If in low doses (10 mg/kg), the analgesic effect of DHCB will be no more obvious than that of morphine but superior to that of THP. While in high doses (40 mg/kg), DHCB will achieve an analgesic effect on heat stimulation close to that of small-dose morphine.

TABLE 2

Thermal Radiation Tail-Flick Experiment in Mice-Analgesic Effect

| | Blank control (normal saline group) | Positive control 1 (morphine, 10 mg/kg) | Positive control 2 (1-THP, 10 mg/kg) | DHCB (5 mg/kg) | DHCB (10 mg/kg) | DHCB (40 mg/kg) |
|---|---|---|---|---|---|---|
| Tail-flick threshold(s) | 8 | 20 | 10 | 9 | 12 | 17 |

Activity Example 4:

Thermal Radiation Tail-flick Experiment II in Mice (Tail-flick Assay): to Evaluate the Duration Time of the Analgesic Effect In Vivo of the Compounds of the Present Invention.

Select CD-1 mice (with the original weight being 30-40 g) and divide them into 6 groups (solvent group, morphine group, and DHCB groups with different doses: 10, 20 and 40 mg/kg), each including 9-11 mice. Place mice tails on the thermal radiation tail-flick apparatus and direct the light beam at ⅓ of the mice tails. First determine the basic pain thresholds of each group of mice, then inject the test samples into the abdominal cavities of the mice respectively, and determine the mice's pain thresholds within 6 hours according to time points. The irradiation time was no more than 22 sec.

Figure 4:
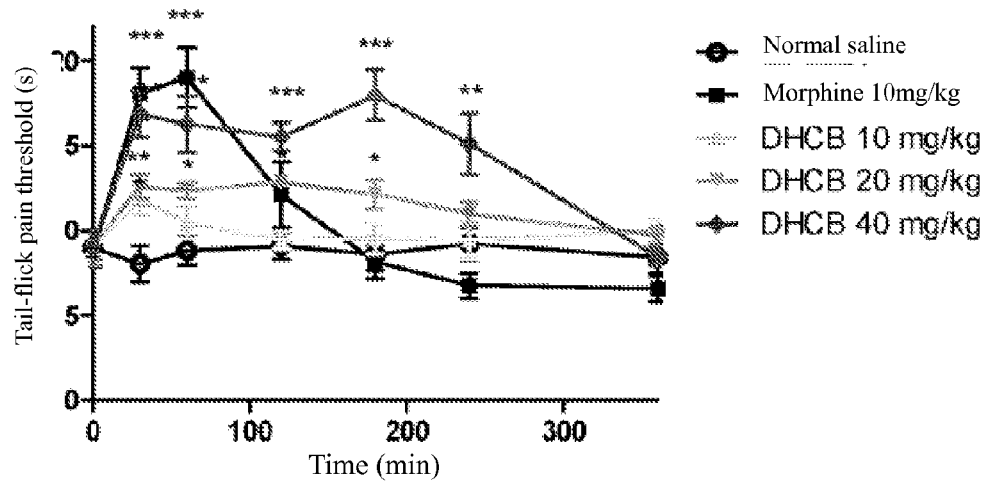
FIG. 4 illustrates the duration time of the analgesic effect of berberine derivative 12 (namely DHCB) in thermal radiation tail-flick experiment in mice.

Experimental results are as shown in FIG. 4, wherein, at the beginning, morphine has stronger analgesic effect, which, however, weakens quickly two hours later, while DHCB, in the doses of 20 and 40 mg/kg, does not exhibit conspicuous attenuation until four hours have passed, which displays more durable effect.

Activity Example 5: to Evaluate the Analgesic Effect In Vivo of the Compounds of the Present Invention Through Formalin Pain Experiment in Mice.

Figure 5:
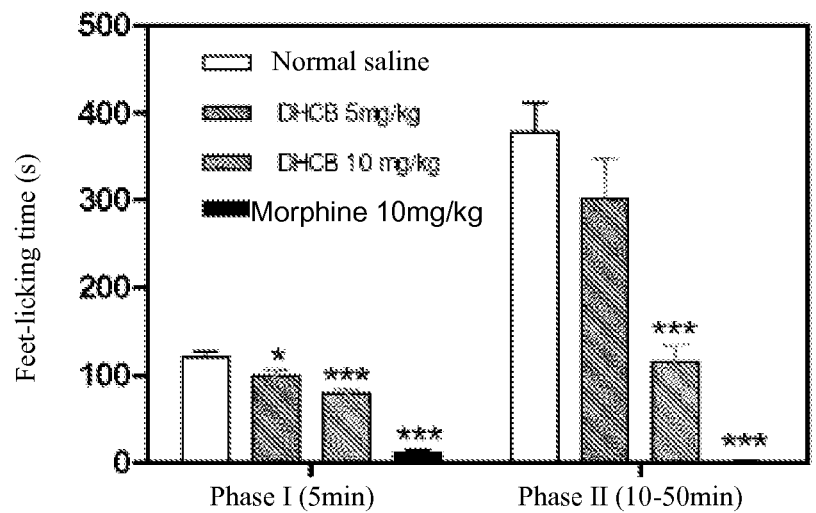
FIG. 5 illustrates the analgesic effect of berberine derivative 12 (namely DHCB) in formalin pain experiment in mice.

Select CD-1 mice (with the original weight being 30-40 g) and divide them into 4 groups (solvent group, morphine group, and DHCB groups with different doses: 5 and 10 mg/kg), each including 9-11 mice. Place hind paws of the mice that are marked with formalin injection into the cages for 15-30 min. Inject drugs of corresponding doses into each mouse, and after 15 min, infuse 5% formalin solution subcutaneously into the underside of marked paw feet. The mice soon began to lick or bite their injected feet. Keep observation for 50 min, and record mice feet-licking time within phase I (0-5 min) and phase II (10-50 min). As shown in FIG. 5, the experimental results show that, DHCB has substantial analgesic effect within phase I of the analgesia model in the doses of 5 mg/kg and 10 mg/kg, and has significant analgesic effect within phase II under the dose of 10 mg/kg, indicating that DHCB acts on both acute and chronic inflammatory pain.

Activity Example 6: Drug Resistance Experiment of DHCB

Figure 6:
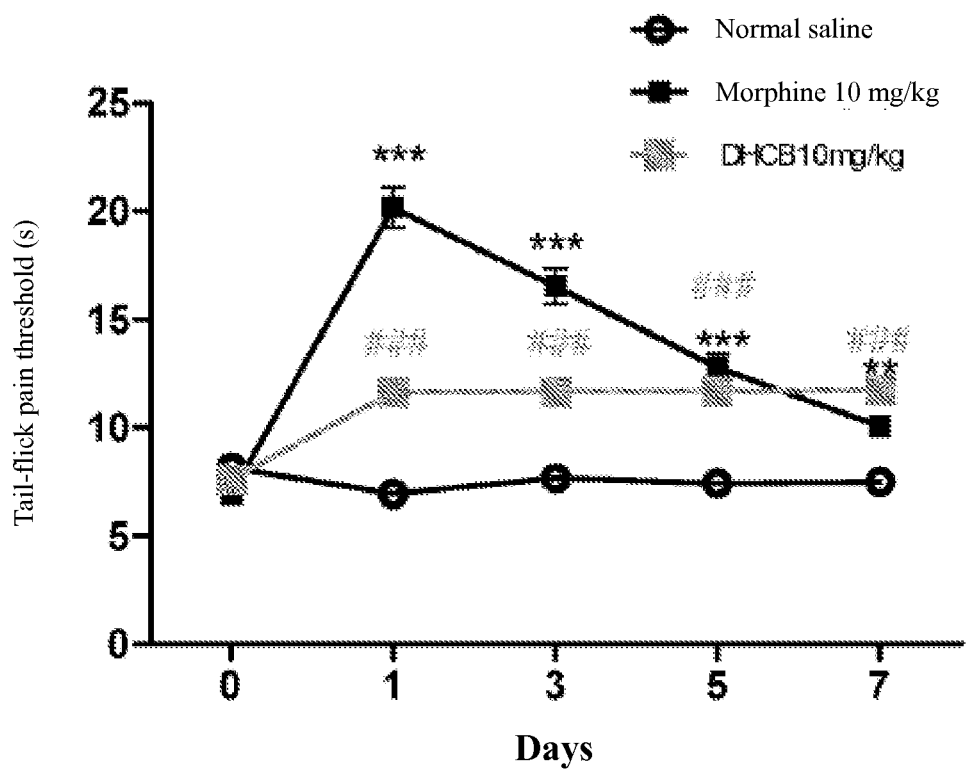
FIG. 6 illustrates the performance of berberine derivative 12 (namely DHCB) in drug resistance experiment.

Drug resistance is a defect existing in many commonly used analgesics, which constitutes great limitations on their use. This experiment studies the drug resistance of DHCB through mice tail-flick under thermal radiation. During the experiment, DHCB (10 mg/kg) had been injected into the abdominal cavity of the mice for successive 7 days and the mice's pain thresholds had been detected every other day. The results as shown in FIG. 6 point out that, DHCB had an unchanged analgesic effect during the 7 days, while by contrast, the analgesic effect of morphine began to reduce obviously from the third day.

What is claimed is:

1. A method of treating pain comprising administering a patient a pharmaceutically effective amount of an isolated or synthesized compound with one of the following formulae:

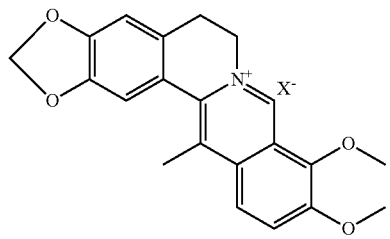

2

3

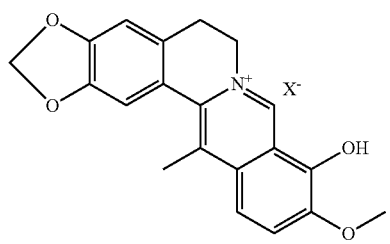

4

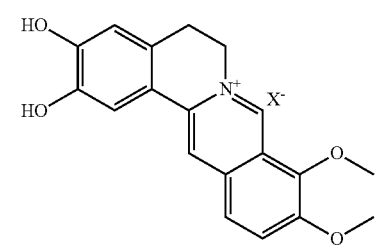

5

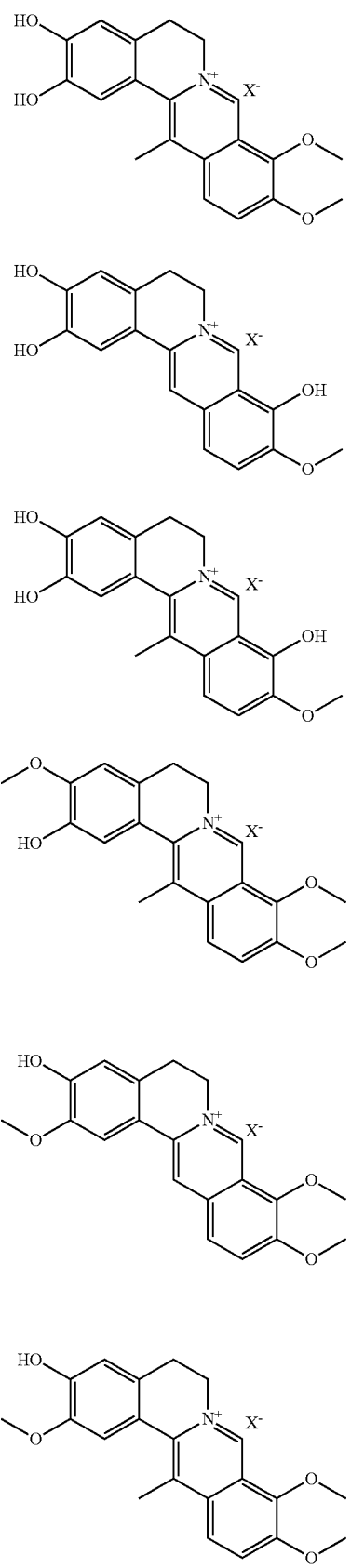
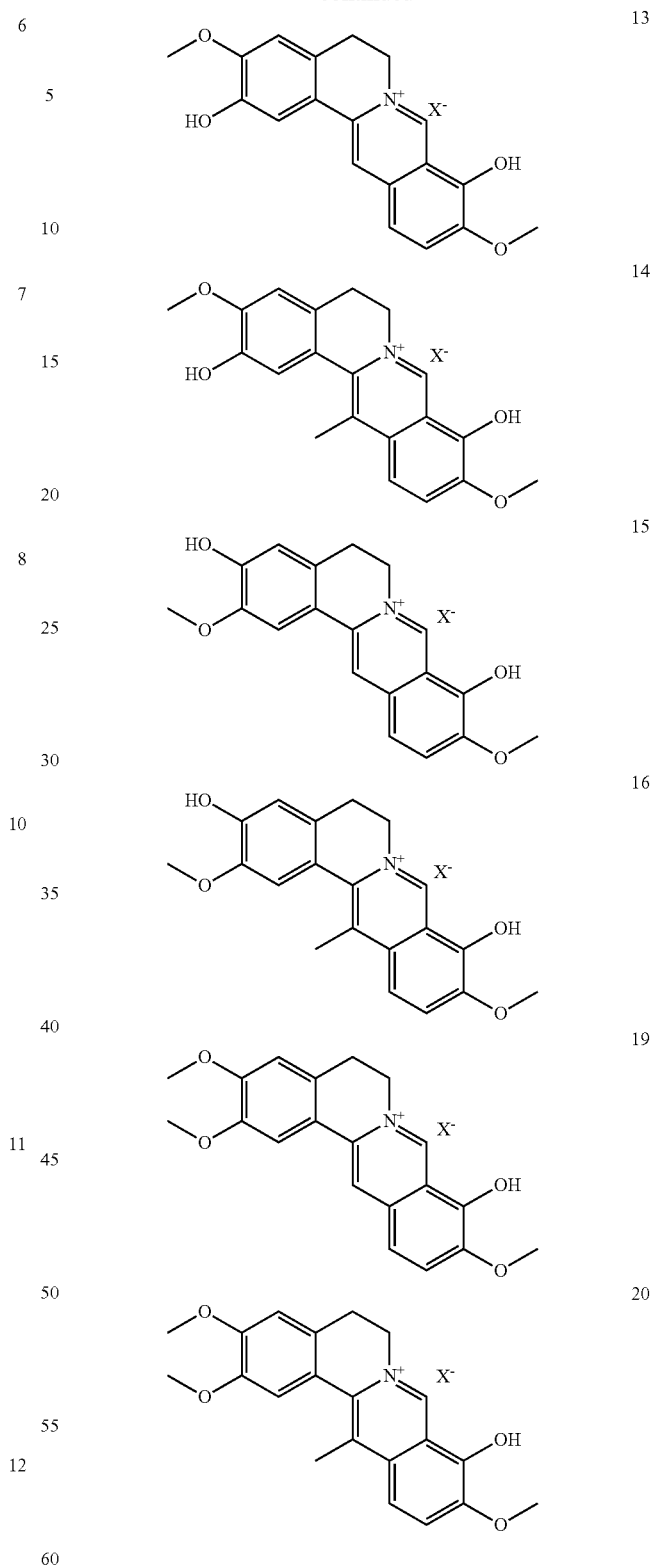
or a pharmaceutical salt, hydrate, or solvate thereof:
wherein,
X is an anion selected from the group consisting of halide ions and carboxylate radicals.
2. The method according to claim 1, wherein the pharmaceutically acceptable salt is a salt formed by the isolated or synthesized compound with hydrochloric acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, aspartic acid or glutamic acid, or a sodium salt, potassium salt, calcium salt or magnesium salt, or a salt formed by the isolated or synthesized compound with arginine, lysine or histidine.

3. The method of claim 1 wherein the isolated or synthesized compound has the following formula:

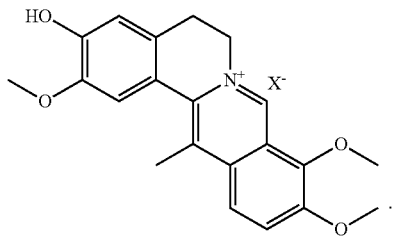

* * * * *